United States Patent [19]

Haber et al.

[11] Patent Number: 5,380,087
[45] Date of Patent: Jan. 10, 1995

[54] PHARMACEUTICAL MIXING CONTAINER WITH ROTATIONALLY MOUNTED HOUSING

[75] Inventors: Terry M. Haber, Lake Forest; Clark B. Foster, Laguna Niguel; William H. Smedley, Lake Elsinore, all of Calif.

[73] Assignee: Habley Medical Technology Corporation, Laguna Hills, Calif.

[21] Appl. No.: 949,596

[22] Filed: Sep. 23, 1992

[51] Int. Cl.$^6$ .................... B01F 11/00; B01F 9/00
[52] U.S. Cl. ..................... 366/130; 366/208; 366/216; 366/237; 206/219; 206/221; 215/DIG. 8; 604/416; 604/903
[58] Field of Search ............... 366/129, 130, 184, 189, 366/197, 203, 204, 208, 209, 210, 212, 213, 216, 219, 220, 232, 237, 347; 215/228, 231, 247, DIG. 3, DIG. 8; 604/201, 228, 232, 416, 903, 56, 82; 206/219, 221

[56] References Cited

U.S. PATENT DOCUMENTS

| | | | |
|---|---|---|---|
| 2,449,968 | 9/1948 | Smith | 604/416 |
| 3,291,454 | 12/1966 | Rosenblatt | 366/213 |
| 3,330,282 | 7/1967 | Visser et al. | 215/DIG. 8 X |
| 4,289,648 | 9/1981 | Hoskins et al. | 604/416 X |
| 4,445,895 | 5/1984 | Margulies | 604/201 X |
| 4,461,578 | 7/1984 | Tiebout | 366/213 |
| 4,848,917 | 7/1989 | Benin et al. | 366/208 |
| 4,850,966 | 7/1989 | Grau et al. | |
| 5,137,528 | 8/1992 | Crose | 604/416 X |

FOREIGN PATENT DOCUMENTS

| | | | |
|---|---|---|---|
| 298067 | 1/1989 | European Pat. Off. | 604/416 |
| 2713678 | 10/1978 | Germany | 366/219 |

Primary Examiner—David A. Scherbel
Assistant Examiner—Charles Cooley
Attorney, Agent, or Firm—Townsend & Townsend Khourie & Crew

[57] ABSTRACT

A pharmaceutical mixing container for storing a liquid having at least two factions which tend to separate during storage. A cartridge housing having an inner volume is closed at one end by a septum arrangement and at another end by a slidable sealing member. The cartridge housing is installed within a cartridge cover having an outwardly extending pitched land. An outer sleeve having a matching pitched groove formed on the inner surface thereof is received about the cartridge cover. The cover is rotationally mounted to a base member. By translating the outer sleeve away from the base member, the cartridge cover and cartridge housing are rotated to provide turbulent mixing action for any liquid within the cartridge housing. In an alternate embodiment, the cartridge cover is omitted and the pitched land is provided directly on the outer surface of the cartridge housing.

13 Claims, 2 Drawing Sheets

PHARMACEUTICAL MIXING CONTAINER WITH ROTATIONALLY MOUNTED HOUSING

BACKGROUND OF THE INVENTION

This invention relates to containers for liquids having a miscible component. More particularly, this invention relates to mixing containers for storing a liquid pharmaceutical.

Containers are known for storing a pharmaceutical having a liquid component and a second component miscible with a liquid component. A typical container of this type is filled with the pharmaceutical and stored for later use. Some pharmaceuticals separate into their individual components when left in storage. For example, liquid NPH insulin has a crystalline faction which must be in solution in order to be effectively administered. During storage in a container, such crystals precipitate out of the liquid solution and must be thoroughly mixed with the liquid faction just prior to administration. Admixture of the crystalline faction and the liquid faction has been achieved in the past in a number of different ways. One such technique is to provide a mixing element which is freely moveable within the container, in a similar manner to the mixing ball found in ordinary aerosol spray cans. This solution has been found to be less than desirable, since the crystalline faction is composed of delicate crystals which should not be mechanically damaged or ruptured during the mixing process. The use of a freely moveable mixing element within the container, however, has been found to damage and rupture the crystals, which severely impairs the effectiveness of the pharmaceutical. Efforts in the past to provide a pharmaceutical mixing container with a freely moveable mixing element devoid of the above disadvantage have not been successful to date.

SUMMARY OF THE INVENTION

The invention comprises a pharmaceutical mixing container which provides thorough admixing of separated components in a pharmaceutical without mechanically damaging those components.

In its broadest aspect, the invention comprises an outer sleeve having a hollow interior with an inner surface, a cartridge housing positioned at least partially within the outer sleeve an arranged for relative motion with respect to said outer sleeve, and means for imparting rotational motion to the cartridge housing when the outer sleeve and the cartridge housing are mutually translated. The cartridge housing has a first end, a second end and a wall structure defining an inner volume for containing the pharmaceutical. A closure member positioned at the first end of the cartridge housing provides a fluid seal at that end; and a sealing member positioned at least partially within the cartridge housing provides a second fluid seal so that the inner volume of the cartridge housing is closed. The closure member for the cartridge housing first end preferably includes a septum and a retaining band for securing the septum to the first end of the housing.

The motion imparting means comprises a mating land and groove formed on the inner surface of the outer sleeve and the outer surface of the cartridge housing, with the groove preferably being formed as an inwardly facing groove in the inner surface of the outer sleeve and the land being formed as an outwardly facing pitched land extending from the outer surface of the cartridge housing. The cartridge housing is preferably rotatably secured to a base member having a central axially extending bore terminating in a first end, with the second end of the cartridge housing being rotatably secured to the first end of the base member.

The outer sleeve preferably includes an end proximate the first end of the base member, and the proximate end of the outer sleeve is releasably secured to the first end of the base member. The outer sleeve and the cartridge housing preferably employ cylindrical geometry.

In an alternate embodiment (not shown), the cartridge housing comprises a cartridge cover having an outer surface and an inner surface, and an inner cartridge received within the cover. In this embodiment, the motion imparting means comprises a mating pitched land and groove formed on the inner surface of the outer sleeve and the outer surface of the cartridge cover.

In use, the liquid is stored within the cartridge housing and is admixed prior to administration by mutually translating the outer sleeve and the cartridge housing while preventing rotation of the base member and the outer sleeve, thereby imparting rotational motion to the cartridge housing. During such motion, turbulent currents are formed within the liquid, thereby admixing the liquid with the miscible component.

After thorough mixing, the liquid may be hydraulically withdrawn from the inner volume of the cartridge housing by penetrating the septum with a needle cannula of a syringe and subsequently operating the syringe. The liquid may also be expelled from the inner volume of the cartridge housing by penetrating the septum with a double point needle and forcibly ejecting the liquid using a drive stem coupled to the sealing member and translating the sealing member with the drive stem in the direction of the first end of the cartridge housing.

While the invention may be employed with a wide variety of miscible pharmaceutical components, it is ideally suited for use with pharmaceuticals having a liquid faction and a crystalline faction requiring gentle admixture prior to use. In particular, the gentle mixing afforded by the turbulent motion in the liquid resulting from the rotation of the cartridge housing is sufficient to thoroughly admix the constituents without damaging the crystal structure.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
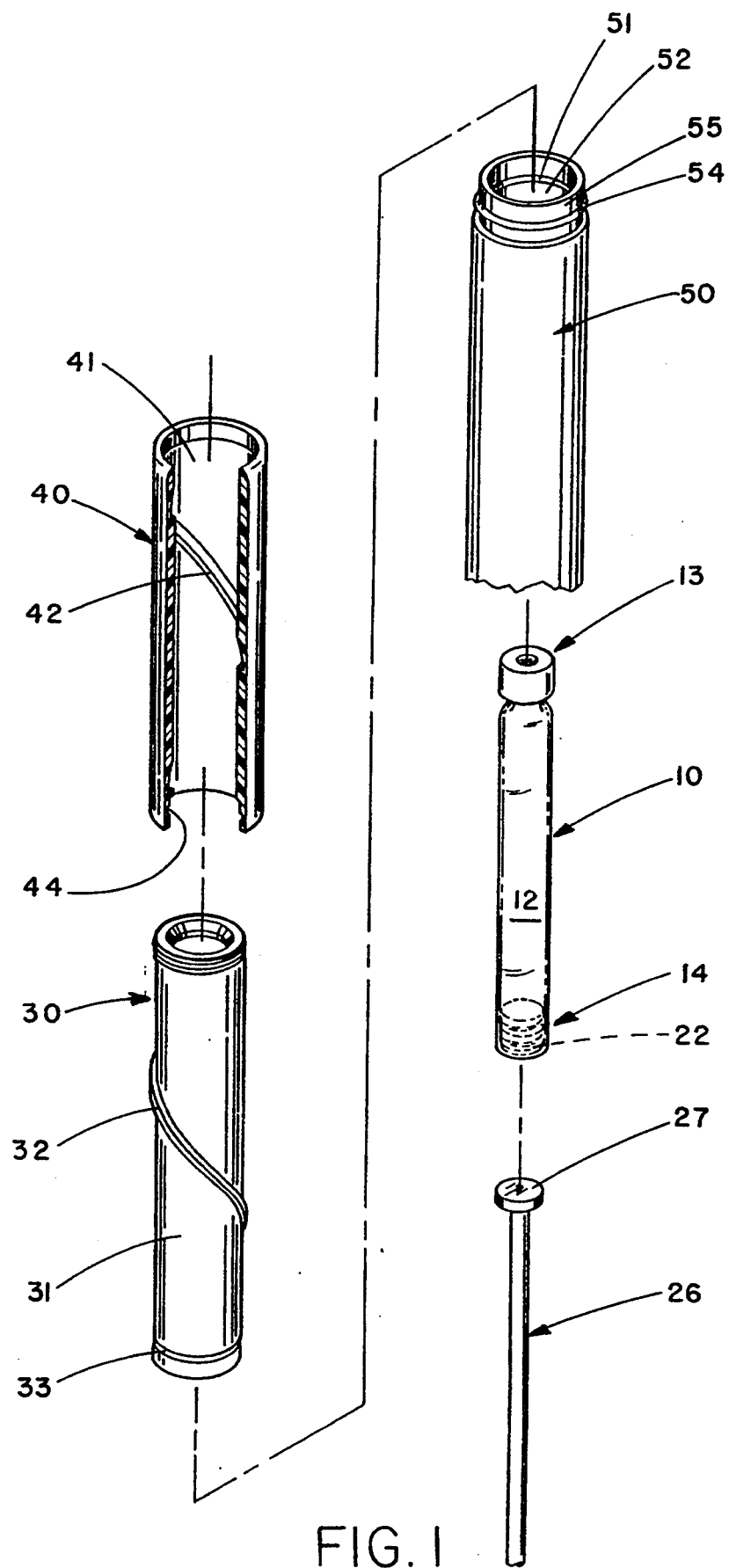
FIG. 1 is an exploded perspective view showing a first embodiment of the invention.
Figures 2, 3:
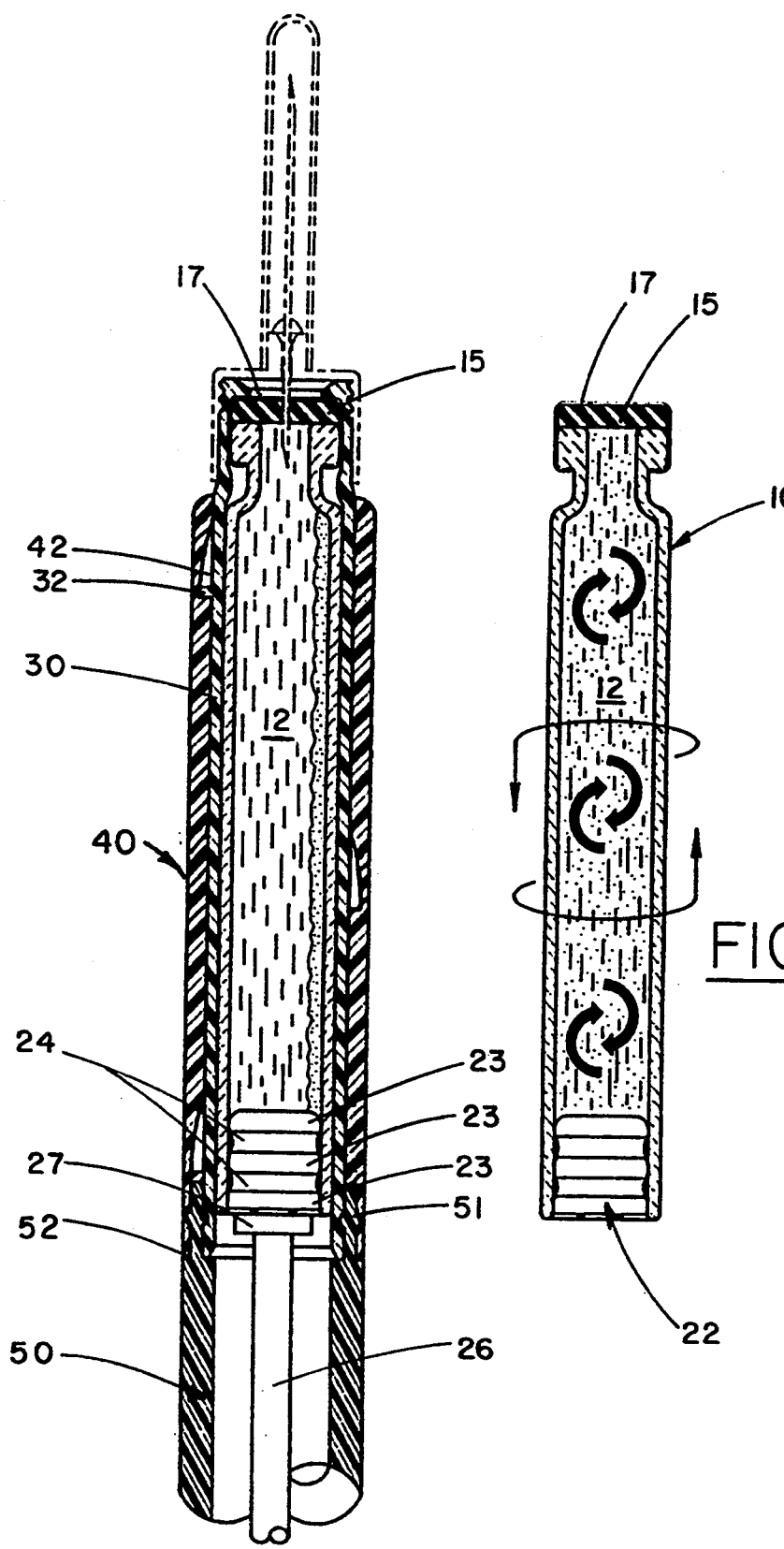
FIG. 2 is a sectional view of the assembled device.
FIG. 3 is a sectional view of the cartridge housing illustrating the rotational motion resulting from the use of the invention of FIG. 1.

Turning now to the drawings, FIGS. 1-3 illustrate a first embodiment of the invention. As seen in these Figs., a cartridge housing generally designated with reference numeral 10 has a generally cylindrical geometrical configuration defining an inner volume 12, a first end 13 and a proximal end 14. Housing 10 may be fabricated from glass or any suitable plastic material which is compatible with the pharmaceutical to be contained therewithin. Secured to distal end 13 is a closure member comprising an elastomeric septum 15 (FIG. 2) which is retained to first end 13 by means of a metal band 17. Septum 15 and band 17 are fabricated and arranged in such a manner that access to the inner volume 12 may be gained by penetrating the band 17 and septum 15 with a needle-like probe, such as a needle cannula of a syringe or a double-ended syringe needle.

A sealing member 22 having an outer diameter providing a sealing engagement with the inner walls of cartridge housing 10 is installed adjacent the proximal end 14 of cartridge housing 10. Sealing member 22 may be fabricated from a wide variety of suitable materials, such as butyl rubber, silicone rubber or the equivalent. Sealing member 22 functions to provide a fluid seal for the proximal end of inner volume 12. For this purpose, sealing member 22 is provided with a plurality of lands 23 and grooves 24 along the outer surface thereof.

A drive stem 26 having a contact end 27 is provided (when desired) to enable manual expulsion of the liquid within inner volume 12 after the liquid has been admixed in the manner described below and is ready to be dispensed. Drive stem 26 may either be mechanically coupled to sealing member 22 by a conventional snap fit arrangement, or may be a detached member.

In the first embodiment, cartridge housing 10 is frictionally received within a cartridge cover generally designated with reference numeral 30 and having an outer wall surface 31 provided with an outwardly extending pitched land 32.

An outer sleeve generally designated with reference numeral 40 has an inner surface 41 provided with a pitched groove 42 having the same pitch angle as land 32. The pitch angle for land 32 and groove 42 is selected to minimize the force required to operate the device, as described below.

Cartridge cover 30 is rotatably mounted to a base member 50 having an inner retaining ring 51 formed on the inner wall surface 52 thereof. Cartridge cover 30 is provided with a corresponding circumferential groove 33 which receives the ring 51 when members 30 and 50 are secured together. The groove 33—ring 51 mechanical combination permits rotation of the cartridge cover 30 without permitting translational motion between the cover 30 and the base 50.

Outer sleeve 40 is provided with a detent groove 44 at the lower end thereof which mates with a circumferential ring 54 formed on the outer surface 55 of base member 50. The groove 44—ring 54 combination provides a releasable detent between outer sleeve 40 and base member 50. Members 30, 40 and 50 are arranged such that translational motion of outer sleeve 40 in the upward direction as viewed in FIG. 1 (or to the right as viewed in FIG. 2) can impart rotational motion to cartridge cover 30 and thus cartridge housing 10 if the user firmly grasps both outer sleeve 40 and base 50. As the outer sleeve 40 and base 50 are translationally separated, the linear motion of outer sleeve 40 is converted to rotary motion of cartridge cover 30 by the land 32—groove 42 coupling. Stated differently, as the outer sleeve 40 is translated away from base 50, slidable motion occurs between groove 42 of outer sleeve 40 and land 32 of cartridge cover 30. Since the cartridge cover is secured against translation by means of the groove 33—ring 51 mechanical coupling but is free to rotate, this sliding motion between land 32 and groove 42 is converted to rotational motion of cartridge cover 30 and thus cartridge housing 10. The rotational motion of the cartridge housing 10 results in turbulence in the liquid as illustrated in FIG. 3 by the curved arrows. This turbulence causes the mixing action within the volume 12.

In use, sealing member 22 is installed from the proximal end of cartridge housing 10. The inner volume 12 is then filled with the pharmaceutical liquid, and septum 15 and closure band 17 are installed to seal volume 12. Thereafter, cartridge 10 is inserted within cover 30, and cover 30 is secured to the upper end of base member 50. Thereafter, outer sleeve 40 is threaded onto outer sleeve 30 until groove 44 makes contact with outer ring 54 formed at the upper end of base member 50.

When the pharmaceutical is to be administered, the user grasps the base 50 about the outer surface and also outer sleeve 40 and then provides a pulling force tending to separate the two elements. This translational motion is converted to rotary motion by the coupling between land 32 and groove 42, thereby causing the cartridge housing 10 to revolve about the longitudinal axis thereof. This rotational motion provides turbulent currents within the liquid so that the constituent ingredients are admixed without mechanically damaging any delicate constituents, such as the crystalline faction found in NPH type insulin. After thorough admixture, the septum 15 is penetrated by means of a needle canula of a syringe or a double point needle, and the liquid is withdrawn from inner volume 12 either hydraulically or by pushing drive stem 26 against sealing member 22 so as to translate sealing member 22 in the direction of distal end 13 of cartridge housing 10.

In an alternate embodiment (not shown), the cartridge cover 30 is dispensed with and the land 32 is formed directly on the outer surface of cartridge housing 10. In this embodiment, the coupling between base member 50, cartridge housing 10 and outer sleeve 40 is essentially that described above with respect to the embodiment of FIGS. 1–3. Operation of this alternative embodiment is essentially identical to that described above, with the exception that the rotational motion is imparted by outer sleeve 40 directly to the cartridge housing 10 (as opposed to indirectly via cartridge cover 30).

As will now be apparent, the invention provides a pharmaceutical mixing container capable of thoroughly admixing the pharmaceutical constituent ingredients in a relatively simple and expedient fashion. In addition, mixing containers fabricated according to the invention are relatively simple and inexpensive to fabricate, can be readily filled with the appropriate liquid pharmaceutical, and can easily be employed for administering the pharmaceutical to a patient.

While the above provides a full and complete disclosure of the preferred embodiments of the invention, various modifications, alternate constructions and equivalents may occur to those skilled in the art. For example, while the rotational motion imparting mechanism has been shown as a matching pitched land and groove formed respectively on the cartridge cover 30 (or the cartridge housing 10) and the inner surface of the outer sleeve 40, a reverse arrangement may be employed, if desired. Similarly, the land 32 can be replaced by a simple outwardly extending protrusion which is capable of sliding within groove 42, as desired. In addition, the slidable sealing member 22 may be omitted in some applications and the inner volume 12 may be sealed by a solid cartridge housing bottom or a wall formed internally of the cartridge housing walls. Therefore, the above descriptions should not be construed as limiting the scope of the invention, which is defined by the appended claims.

What is claimed is:

1. A pharmaceutical mixing container for storing a liquid with a miscible component, said container comprising:
   an outer sleeve having a longitudinal axis and a hollow interior with an inner surface;
   a cartridge housing positioned at least partially within said outer sleeve and arranged for relative motion with respect thereto, said cartridge housing having a first end, a second end and a wall structure defining an inner volume;
   a closure member at said first end providing a fluid seal;
   means for providing a second fluid seal adjacent said second end; and
   means for imparting rotational motion to said cartridge housing when said outer sleeve is translated relative to the cartridge housing in a direction of the longitudinal axis so that the liquid and the miscible component can be admixed by the rotational motion of said cartridge housing.

2. The invention of claim 1 wherein: said closure member comprises a septum.

3. The invention of claim 2 wherein: said closure member further includes a retaining band.

4. The invention of claim 1 wherein: said outer sleeve and said cartridge housing have cylindrical geometry.

5. The invention of claim 1 wherein: said fluid seal providing means comprises a sealing member at least partially positioned within said cartridge housing.

6. The invention of claim 5 further comprising: means for enabling the liquid within the container to be ejected from said first end when said closure member is opened.

7. The invention of claim 6 wherein: said sealing member is slidably received by said cartridge housing; and wherein said enabling means comprises a drive stem coupled to said sealing member.

8. The invention of claim 1 further comprising: a base member having a central bore terminating at a first end; and
   said second end of said cartridge housing being rotatably coupled to said first end of said base member.

9. The invention of claim 1, wherein:
   the rotational motion imparting means imparts a rotational motion about the longitudinal axis.

10. A Pharmaceutical mixing container for storing a liquid with a miscible component, said container comprising:
   an outer sleeve having a hollow interior with an inner surface;
   a cartridge housing positioned at least partially within said outer sleeve and arranged for relative motion with respect thereto, said cartridge housing having a first end, a second end, an outer surface and a wall structure defining an inner volume;
   a closure member at said first end providing a fluid seal;
   means for providing a second fluid seal adjacent said second end so that said inner volume is closed; and
   means for imparting rotational motion to said cartridge housing when said outer sleeve is translated relative to the cartridge housing so that the liquid and the miscible component can be admixed by the rotational motion of said cartridge housing, said rotational motion imparting means comprising a mating land and groove, the groove being formed on said inner surface of said outer sleeve and the land being coupled to said outer surface of said cartridge housing.

11. A pharmaceutical mixing container for storing a liquid with a miscible component, said container comprising:
   an outer sleeve having a hollow interior with an inner surface;
   a cartridge housing positioned at least partially within said outer sleeve and arranged for relative motion with respect thereto, said cartridges housing having a first end, a second end, an outer surface, and a wall structure defining an inner volume;
   a closure member at said first end providing a fluid seal;
   means for providing a second fluid seal adjacent said second end so that said inner volume is closed; and
   means for imparting rotational motion to said cartridge housing when said outer sleeve is translated relative to the cartridge housing so that the liquid and the miscible component can be admixed by the rotational of motion said cartridge housing, said motion imparting means comprising an outwardly facing land coupled to said outer surface of said cartridge housing and an inwardly facing groove formed in the inner surface of said outer sleeve.

12. A pharmaceutical mixing container for storing a liquid with a miscible component, said container comprising:
   an outer sleeve having a hollow interior with an inner surface;
   a cartridge housing positioned at least partially within said outer sleeve and arranged for relative motion with respect thereto, said cartridge housing having a first end, a second end, an outer surface and a wall structure defining an inner volume;
   a closure member at said first end providing a fluid seal;
   means for providing a second fluid adjacent said second end so that said inner volume is closed;
   means for imparting rotational motion to said cartridge housing when said outer sleeve is translated relative to the cartridge housing so that the liquid and the miscible component can be admixed by the rotational motion of said cartridge housing; and
   a base member having a central bore terminating at a first end;
   said second end of said cartridge housing being rotatably coupled to said first end of said base member;
   the outer sleeve having an end proximate said first end of said base member, said end of said outer sleeve being releasably secured to said first end of said base member.

13. A Pharmaceutical mixing container for storing a liquid with a miscible component, said container comprising:
   an outer sleeve having a hollow interior with an inner surface;
   a cartridge housing positioned at least partially within said outer sleeve and arranged for relative motion with respect thereto, said cartridge housing having a first end, a second end, an outer surface and a wall structure defining an inner volume;

a closure member at said first end providing a fluid seal;

means for providing a second fluid seal adjacent said second end so that said inner volume is closed; and means for imparting rotational motion to said cartridge housing when said outer sleeve is translated relative to the cartridge housing so that the liquid and the miscible component can be admixed by the rotational motion of said cartridge housing, said rotational motion imparting means including a cartridge cover having an outer surface and an inner surface, the cartridge housing being received within said cartridge cover, said rotational motion imparting means also including a mating land and a groove, the grove being formed on said inner surface of said outer sleeve and the land being formed on said outer surface of said cartridge cover.

* * * * *